(12) United States Patent
Montgomery et al.

(10) Patent No.: US 10,960,169 B2
(45) Date of Patent: *Mar. 30, 2021

(54) SYSTEM AND METHOD OF ADMINISTERING A PHARMACEUTICAL GAS TO A PATIENT

(71) Applicant: Mallinckrodt Hospital Products IP Limited, Dublin (IE)

(72) Inventors: Frederick J. Montgomery, Sun Prairie, WI (US); Duncan P. Bathe, Fitchburg, WI (US)

(73) Assignee: Mallinckrodt Hospital Products IP Limited, Dublin (IE)

(*) Notice: Subject to any disclaimer, the term of this patent is extended or adjusted under 35 U.S.C. 154(b) by 0 days.

This patent is subject to a terminal disclaimer.

(21) Appl. No.: 16/156,453

(22) Filed: Oct. 10, 2018

(65) Prior Publication Data

US 2019/0038864 A1    Feb. 7, 2019

Related U.S. Application Data

(63) Continuation of application No. 14/551,186, filed on Nov. 24, 2014, now Pat. No. 10,099,029, which is a
(Continued)

(51) Int. Cl.
*A61M 16/00* (2006.01)
*A61M 16/12* (2006.01)
(Continued)

(52) U.S. Cl.
CPC ........ *A61M 16/12* (2013.01); *A61M 16/0003* (2014.02); *A61M 16/0051* (2013.01);
(Continued)

(58) Field of Classification Search
CPC .............. A61M 16/12; A61M 16/0003; A61M 16/0051; A61M 16/024; A61M 16/04; A61M 16/0666; A61M 16/105; A61M 16/16; A61M 16/201; A61M 16/107; A61M 2016/003; A61M 2016/0015; A61M 2016/0021; A61M 2016/0027; A61M 2016/0039; A61M 2202/0233; A61M 2202/0275; A61M 2205/18;
(Continued)

(56) References Cited

U.S. PATENT DOCUMENTS 6,786,217 B2 * 9/2004 Stenzler .............. A61M 16/203
                                                        128/204.23

* cited by examiner

*Primary Examiner* — Steven O Douglas
(74) *Attorney, Agent, or Firm* — Servilla Whitney LLC

(57) ABSTRACT

Methods and systems for delivering a pharmaceutical gas to a patient. The methods and systems provide a known desired quantity of the pharmaceutical gas to the patient independent of the respiratory pattern of the patient over a plurality of breaths every $n^{th}$ breath, where n is greater than or equal to 1. The pharmaceutical gases include CO and NO, both of which are provided as a concentration in a carrier gas. The gas control system determines the delivery of the pharmaceutical gas to the patient to result in the known desired quantity (e.g. in molecules, milligrams or other quantified units) of the pharmaceutical gas being delivered. Upon completion of that known desired quantity of pharmaceutical gas over a plurality of breaths, the system can either terminate, continue, activate and alarm, etc.

20 Claims, 5 Drawing Sheets

Related U.S. Application Data continuation of application No. 13/331,807, filed on Dec. 20, 2011, now Pat. No. 8,893,717, which is a continuation-in-part of application No. 12/430,220, filed on Apr. 27, 2009, now Pat. No. 8,091,549, and a continuation-in-part of application No. 13/287,663, filed on Nov. 2, 2011, now Pat. No. 8,517,015, and a continuation of application No. 13/284,433, filed on Oct. 28, 2011, now Pat. No. 8,397,721, which is a continuation of application No. 11/231,554, filed on Sep. 21, 2008, now Pat. No. 7,523,752.

(51) Int. Cl.
| | | |
|---|---|---|
| *A61M 16/20* | (2006.01) | |
| *A61M 16/04* | (2006.01) | |
| *A61M 16/06* | (2006.01) | |
| *A61M 16/10* | (2006.01) | |

(52) U.S. Cl.
CPC .......... *A61M 16/024* (2017.08); *A61M 16/04* (2013.01); *A61M 16/0666* (2013.01); *A61M 16/105* (2013.01); *A61M 16/201* (2014.02); *A61M 16/107* (2014.02); *A61M 2016/003* (2013.01); *A61M 2016/0015* (2013.01); *A61M 2016/0021* (2013.01); *A61M 2016/0027* (2013.01); *A61M 2016/0039* (2013.01); *A61M 2202/0233* (2013.01); *A61M 2202/0275* (2013.01); *A61M 2205/18* (2013.01); *A61M 2205/3334* (2013.01); *A61M 2205/50* (2013.01); *A61M 2205/75* (2013.01)

(58) Field of Classification Search
CPC ...... A61M 2205/3334; A61M 2205/50; A61M 2205/75
See application file for complete search history.

SYSTEM AND METHOD OF ADMINISTERING A PHARMACEUTICAL GAS TO A PATIENT

CROSS-REFERENCE TO RELATED APPLICATIONS

This application is a continuation under 35 U.S.C. § 120 of U.S. patent application Ser. No. 14/551,186, filed Nov. 24, 2014, which is a continuation under 35 U.S.C. § 120 of U.S. patent application Ser. No. 13/331,807, filed Dec. 20, 2011, now U.S. Pat. No. 8,893,717, issued Nov. 25, 2014, which is a continuation-in-part under 35 U.S.C. § 120 of U.S. patent application Ser. No. 12/430,220, filed Apr. 27, 2009, now U.S. Pat. No. 8,091,549, issued Jan. 10, 2012, and U.S. patent application Ser. No. 13/287,663, filed Nov. 2, 2011, now U.S. Pat. No. 8,517,015, issued Aug. 27, 2013, and U.S. patent application Ser. No. 13/284,433, filed Oct. 28, 2011, now U.S. Pat. No. 8,397,721, issued Mar. 19, 2013, which are continuations of U.S. patent application Ser. No. 11/231,554, filed Sep. 21, 2005, now U.S. Pat. No. 7,523,752, issued Apr. 28, 2009, the entire disclosures of which are hereby incorporated by reference herein.

BACKGROUND

The present invention relates to methods and systems for administering a pharmaceutical gas to a patient and, more particularly, to methods and systems for introducing carbon monoxide CO or nitric oxide NO to a patient in a predetermined quantity.

The normal or conventional way of giving a pharmaceutical drug to a patient is to prescribe the dose based on the quantity of drug (usually in weight) per unit weight of the patient (e.g. mg/Kg) with the dose being specified to be delivered over a period of time or being repeated at specified intervals of time. This allows the user to control the quantity of drug and ensures the quantity of drug being delivered is in proportion to the patient's size. This is to reduce the patient to patient variability in response to the drug due to the size of the patient i.e. a 7 Kg baby will not get the same quantity of drug as a 80 Kg adult.

In recent times there have been a number of gases which have been shown to have pharmaceutical action in humans and animals. Examples include Nitric Oxide (NO) Zapol et al U.S. Pat. No. 5,485,827 and more recently Carbon Monoxide (CO) Otterbein et al (U.S. Published Patent Application No. 2003/0219496). In the Otterbein patent application, CO is described as having a pharmacological action in a number of medical conditions including ileus and vascular disease.

In these cases, the carbon monoxide gas needs to be delivered to the patients' alveoli where it can move across the alveolar membrane and into the blood stream where its action can take effect. The current dosing used in these cases is for the patient to breath at a specified concentration of CO in ppm for a specified period of time. Accurate dosing of CO for these treatments is important as CO reacts with the hemoglobin in the blood to form carboxyhemoglobin which means the hemoglobin is no longer able to carry oxygen to the tissues of the body. If too much CO is given, the patient may exhibit the toxic effects of CO for which it is usually known.

There is a tight window for CO delivery between the therapeutic level and the level that causes carboxyhemoglobin above safe levels. Up until now CO has been delivered as a constant concentration in the gas breathed by the patient/animal for a specified period of time. For example in reference 3 of the Otterbein publication, (Example 2 pg 13) the therapeutic dose delivered to mice for the treatment of ileus was 250 ppm of CO for 1 hour.

However, this method of dosing CO can be associated with large variability in the actual dose being delivered to the animal/humans alveoli. This variability is because the quantity of CO being delivered to the animal/patient is dependent on a number of variables including, but not limited to, the patients tidal volume, respiratory rate, diffusion rate across the alveolar and ventilation/perfusion (V/Q) matching.

The amount of CO delivered into a patient's alveoli can be determined by the ideal gas law as shown in the following equation:

$$N = PV/(R_u T) \quad (1)$$

Where: N is the number of moles of the gas (mole) P is the absolute pressure of the gas (joule/m$^3$) V is the volume of the particular gas (m$^3$), $R_u$ is the universal gas constant, 8.315 joule/mole-K and T is the absolute temperature (K).

If we assume atmospheric pressure (101,315 joule/m$^3$) and 20° C. (293 K) as the temperature and we express the volume in mL (10$^{-6}$ m$^3$), then equation (1) reduces to:

$$N = 4.16 \times 10^{-5} V \text{ (moles)} \quad (2)$$

Equation (2) can be used to calculate the number of moles of gas delivered to a patient's alveolar volume over a period of time when given a specified concentration by using the following equation:

$$N_{CO} = RR \cdot t \cdot C_{CO} \cdot 10^{-6} \cdot 4.16 \times 10^{-5} V_a \quad (3)$$

Where; $C_{CO}$ is the concentration of CO (ppm), $V_a$ is the alveolar volume (mL), RR is the respiratory rate (BPM) and t is the time in minutes.

For example, if the CO dose for ileus in humans was 250 ppm of CO for one hour (60 minutes), the alveolar volume is 300 mL and the patients respiratory rate is 12 breaths per minute (bpm) then the amount of CO gas in moles delivered to the patients alveoli over that period would be:

$$N_{CO} = 12 \cdot 60 \cdot 250 \cdot 10^{-6} \cdot 4.16 \times 10^{-5} \cdot 300 = 2.25 \times 10^{-3} \text{ moles}$$

This can be converted into the mass of drug delivered ($M_{CO}$) using the gram molecular weight of CO which is 28 as shown in the following equation:

$$M_{CO} = N_{CO} \cdot 28 = 63 \times 10^{-3} \text{ g} = 63 \text{ mg} \quad (4)$$

However, although this works for a given set of assumptions, a spontaneous patient's respiratory rate can vary widely from perhaps 8 to 20 breaths per minute depending on circumstances and the patient's alveolar volume per breath can also vary significantly from say 200 to 400 mL depending on the metabolic need. These variables can have a dramatic effect on the amount of gaseous drug being delivered to the patient over the same period of time. For instance, if the patients respiratory rate was 8 bpm and the alveolar volume was 200 mL, the CO dose delivered to the patients alveoli would have been 27.8 (mg). Likewise if the patients respiratory rate was 20 bpm and the alveolar volume was 400 mL, then the dose delivered to the patients alveoli would have been 139.2 (mg) thus representing a five-fold difference in the amount of drug being delivered.

This means, in the example of CO, the quantity of gaseous drug a patient gets as measured in grams could vary substantially depending on the patient's ventilation pattern. For a dose based on constant concentration and time, the effect of these variables could mean that an individual patient could get significantly higher or lower doses of CO in grams and this could result in either high unsafe levels of carboxyhemoglobin or doses too low to be effective. Although not all the gaseous drug delivered to the alveoli will be taken up by the body's bloodstream (due to variables such as cardiac output and the diffusion coefficient of the gas) controlling the amount delivered to the alveoli takes away a major source of variability.

In addition, there is a need to administer NO to a patient in a predetermined quantity as described in "Cell-free hemoglobin limits nitric oxide bioavailabllity in sickle-cell disease", Nature Medicine, Volume 8, Number 12, December 2002, pages 1383 et seq. This paper describes the use of inhaled NO to react with cell free hemoglobin to form plasma methemoglobin and so reduce the ability of the cell free hemoglobin in the plasma to consume endogenously produced NO (FIG. 5, page 1386). The quantity of NO delivered to the patient blood needs to be equivalent to the amount of cell free hemoglobin that is in the patients plasma. The amount of NO delivered to a sample of sickle cell patients was 80 ppm of NO for 1.5 hours. However, there was variability in the amount of methemoglobin produced in individual patients as shown by the error bars on FIG. 4b. So, in a similar way to the CO example, a known quantity of NO needs to be delivered to a patient to provide the desired therapeutic effect and again it is important to remove any variability of delivery because of differences in the individual patient's respiratory pattern.

Accordingly, it would be advantageous to have a system and method of introducing pharmaceutical gases (such as carbon monoxide and nitric oxide) that allows for the precise control of a known quantity of the pharmaceutical gas to be delivered to the patients alveoli and which is not subject to change based on the patients respiratory patterns.

SUMMARY

Accordingly, the present invention relates to systems and methods for administering a pharmaceutical gas, such as carbon monoxide and nitric oxide, that allows a clinician to determine and control the desired quantity of the gas to be delivered to the patient. The methods determine the desired quantity of the pharmaceutical gas to be administered to the patient and then administers the desired quantity of the pharmaceutical gas irrespective of the patients respiratory patterns. If the prescription is specified as a total quantity of drug, then the method terminates the administration of the pharmaceutical gas when the desired total quantity has been administered to the patient.

Thus, by the methods of various embodiments of the present invention, the amount of the pharmaceutical gas is delivered to the patient as a known desired quantity and that known desired quantity can be expressed in various units of measurement, such as, but not limited to, the weight of drug in micrograms (µg), milligrams (mg), grams (g) etc., the moles of drug in nanomoles (nM), micromoles (µM), millimoles (mM) moles (M) etc, or the volume of drug, at a known concentration or partial pressure, in microliters (µL), milliliters (mL), liters (L) etc. The desired quantity of the pharmaceutical gas can also be expressed as an amount per unit of time for a period of time such as mg/hour for 2 hours.

One or more embodiments of the invention also include systems for administering a pharmaceutical gas, such as carbon monoxide or nitric oxide, and the system includes an inlet means that can be connected to the source of the pharmaceutical gas and deliver the gas to a patient by means of a patient device. That patient device can be any device that actually introduces the pharmaceutical gas into the patient such as a nasal cannula, endotracheal tube, face mask or the like. There is also a gas control system that controls the introduction of the quantity of a pharmaceutical gas from the gas source through the patient device. Again, therefore, the system provides a known quantity of gas to the patient.

As such, embodiments of the present invention allows a user to set a desired quantity of gaseous drug to be delivered to a patient's alveoli and for the system to then deliver that gaseous drug over multiple breaths until the prescribed amount has been delivered.

As a further embodiment, the system and method may simply provide an alarm, visual and/or audible, to alert the user when the predetermined total quantity of the pharmaceutical gas has been administered to the patient and not actually terminate that administration. As such, the user is warned that the total predetermined desired quantity administered over the plurality of breaths has now been delivered to the patient so that the user can take the appropriate action, including a closer monitoring of the patient.

These and other features and advantages of the present invention will become more readily apparent during the following detailed description taken in conjunction with the drawings herein.

One or more embodiments of the invention are directed to methods of administering a therapy gas to a patient, the therapy gas being at least one gas selected from CO and NO. The methods comprise determining a desired total quantity of therapy gas to be administered to the patient over a period of time over a plurality of breaths. A quantity of the therapy gas is administered to the patient during inspiration every $n^{th}$ breath of the plurality of breaths, wherein n is 1 or greater. The quantity of the therapy gas varied per $n^{th}$ breath to ensure that the desired total quantity over the period of time is administered independent of the respiratory pattern of the patient.

In some embodiments, the quantity of therapy gas per $n^{th}$ breath is in the range of a minimum quantity of therapy gas per breath and a maximum quantity of therapy gas per breath. In detailed embodiments, the quantity of therapy gas per nth breath is a function of one or more of a first respiratory rate, a first tidal volume of the patient and the patient's ideal body weight. In specific embodiments, the quantity of therapy gas per $n^{th}$ breath to be delivered is greater than the minimum quantity of therapy gas per breath and less than the maximum quantity of therapy gas per breath, the quantity of therapy gas per breath is administered on the $n^{th}$ breath, or when the quantity of therapy gas per nth breath is less than the minimum quantity of therapy gas per breath, administration of the quantity of therapy gas per nth breath is skipped for that $n^{th}$ breath, or when the quantity of therapy gas per $n^{th}$ breath is greater than the maximum quantity of therapy gas per breath, one or more of an alarm is triggered or the maximum quantity is delivered on the nth breath and a difference between the quantity of therapy gas per $n^{th}$ breath to be delivered and the maximum quantity of therapy gas per breath is carried to one or more subsequent breaths. In certain embodiments, when the quantity of therapy gas per $n^{th}$ breath is skipped, a new quantity of therapy gas per $n^{th}$ breath is calculated. In detailed embodiments, when the quantity of therapy gas per $n^{th}$ breath is greater than the maximum quantity of therapy gas per breath, the maximum quantity of therapy gas per breath is administered on the $n^{th}$ breath and the difference between the quantity of therapy gas per $n^{th}$ breath and the maximum quantity of therapy gas per breath is added to one or more subsequent breaths.

In one or more embodiments, n is 2 or greater and the therapy gas is delivered during the $n^{th}$ breath. In some embodiments, no therapy gas is administered during the breaths that are not $n^{th}$ breaths. In detailed embodiments, the quantity of therapy gas per $n^{th}$ breath is in the range of a minimum quantity of therapy gas per breath and a maximum quantity of therapy gas per breath. In specific embodiments, the quantity of therapy gas per $n^{th}$ breath is a function of one or more of a first respiratory rate, a first tidal volume of the patient and the patient's ideal body weight.

In some embodiments, when the quantity of therapy gas per $n^{th}$ breath to be delivered is greater than the minimum quantity of therapy gas per breath and less than the maximum quantity of therapy gas per breath, the quantity of therapy gas per $n^{th}$ breath is administered on the $n^{th}$ breath, or when the quantity of therapy gas per $n^{th}$ breath is less than the minimum quantity of therapy gas per breath, administration of the quantity of therapy gas per $n^{th}$ breath is skipped for that $n^{th}$ breath, or when the quantity of therapy gas per $n^{th}$ breath is greater than the maximum quantity of therapy gas per breath, one or more of an alarm is triggered or the maximum quantity is delivered on the $n^{th}$ breath and a difference between the quantity of therapy gas per $n^{th}$ breath to be delivered and the maximum quantity of therapy gas per breath is carried to one or more subsequent breaths. In one or more embodiments, when the quantity of therapy gas per $n^{th}$ breath is skipped, a new quantity of therapy gas per $n^{th}$ breath is calculated. Detailed embodiments further comprise repeating the administration of the therapy gas on one or more subsequent breaths. In specific embodiments, when the quantity of therapy gas per $n^{th}$ breath is greater than the maximum quantity of therapy gas per breath, the maximum quantity of therapy gas per breath is administered on the $n^{th}$ breath and the difference between the quantity of therapy gas per nth breath and the maximum quantity of therapy gas per breath is added to one or more subsequent breaths. Certain embodiments further comprise repeating the administration of the therapy gas on one or more subsequent breaths.

In some embodiments, when the quantity of therapy gas per nth breath is greater than the maximum quantity of therapy gas per breath, the maximum quantity of therapy gas per breath is administered on the $n^{th}$ breath and the difference between the quantity of therapy gas per $n^{th}$ breath and the maximum quantity of therapy gas per breath is administered over one or more subsequent breaths that are not an $n^{th}$ breath. In specific embodiments, the therapy gas is delivered to the patient's alveoli. In certain embodiments, the therapy gas is delivered to the patient during the first half of the inspiratory cycle.

Additional embodiments are directed to methods of administering a therapy gas to a patient, the therapy gas being at least one of CO and NO. A desired total quantity of therapy gas to be administered to the patient over a period of time over a plurality of breaths is determined. A quantity of therapy gas to be delivered to the patient per $n^{th}$ breath is calculated, where calculating the quantity based on one or more of respiratory rate and quantity already given to the patient. The quantity of the therapy gas administered to the patient's alveoli during the first half of the inspiratory cycle for every $n^{th}$ breath of the plurality of breaths, n being greater than 1 averaged over the period of time. Steps b) and c) are repeated varying the quantity of the therapy gas per $n^{th}$ breath to ensure that the desired total quantity over the period of time is maintained independent of the respiratory pattern of the patient.

Some embodiments further comprise comparing the quantity of therapy gas to be delivered to determine if the quantity is in the range of a minimum quantity and a maximum quantity. In detailed embodiments, if the quantity of therapy gas to be delivered is lower than the minimum quantity, then the quantity of therapy gas delivered during the breath is zero and the quantity of therapy gas to be delivered is added to one or more subsequent breaths. In specific embodiments, wherein if the quantity of therapy gas to be delivered is greater than the maximum quantity, then performing one or more of activating an alarm, determining the difference between the quantity of therapy gas to be delivered and the maximum quantity, administering the maximum quantity or adding the difference between the quantity of therapy gas to be delivered and the maximum quantity to one or more subsequent breaths.

Further embodiments of the invention are directed to systems for administering a therapy gas to a patient having a respiratory pattern, the therapy gas being at least one gas selected from CO and NO. The system comprises an inlet to connect to a source of therapy gas, an outlet to connect to a device that introduces the therapy gas to the patient, a setting control to determine the desired quantity of therapy gas to be delivered to the patient over a plurality of breaths, and a gas control system to deliver the desired quantity of the therapy gas to the patient during inspiration by the patient over the plurality of breaths independent of the patient's respiratory pattern. The gas control system is configured to calculate a quantity of therapy gas to be delivered to the patient per $n^{th}$ breath, calculating the quantity based on one or more of respiratory rate and quantity already given to the patient, administer the quantity of the therapy gas to the patient's alveoli during the first half of the inspiratory cycle for every $n^{th}$ breath of the plurality of breaths, n being greater than 1 averaged over the period of time, and repeat steps a) and b) varying the quantity of the therapy gas per breath to ensure that the desired total quantity over the period of time is maintained independent of the respiratory pattern of the patient.

DETAILED DESCRIPTION

Figure 1:
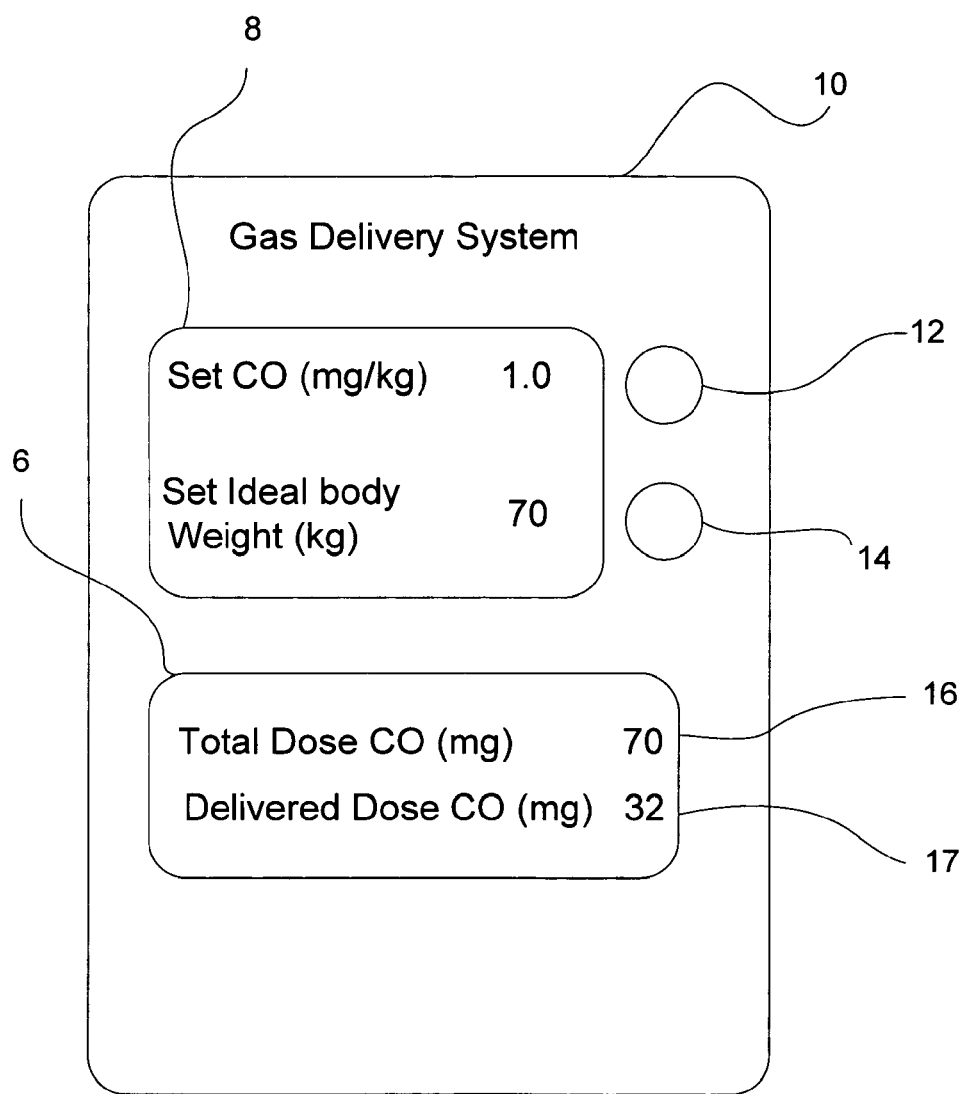
FIGS. 1 and 2 are views of a front panel of an apparatus for carrying out the present invention showing different user options.

In the following detailed description, CO is used as the pharmaceutical gas but the description can also be valid for NO. Referring now to FIG. 1, there is shown a front view of an apparatus that can be used in carrying out the present invention. As can be seen, there is a front panel 10 that can be a part of the apparatus and on that panel there are input setting knobs and displays which allow the user to set and monitor the amount of CO that is to be delivered to the patient.

The means for determining the desired quantity of CO to be delivered is by means of an input setting knob 12 with the set amount being shown on the setting display 8. The units shown in FIG. 1 are in milligrams per kilogram that is, the units are measured in a dosage per kilogram of the patient's ideal body weight. Along with that input, there is a further input 14 whereby the user can enter the patient's ideal body weight in kilograms with the amount also displayed on the setting display 8. With those inputs, the user can set the quantity of the pharmaceutical gas to be administered to the patient in proportion to the size of the patient and which reduces the patient to patient variability in response to the pharmaceutical gas due to the size of the patient, i.e. a 7 kilogram baby will not be administered the same quantity of the pharmaceutical gas as a 80 kilogram adult.

The front panel 10 also has a monitor display 6 which can display total dose of CO (mg) to be delivered (shown at 16) as calculated for multiplying the dosage/kg by the patients ideal body weight in kg.

Once the desired quantity of gaseous drug has been set on the device the system then determines the amount of pharmaceutical gas that is to be delivered in each breath and the amount of time and/or the number of breaths that it will take to deliver the total desired quantity of drug. The monitor display 6 can also display a running total of the delivered dose of CO (mg) (shown at 17) as it is delivered to the patient so the user can monitor the progress of the treatment. This can be updated each breath as more pharmaceutical gas is delivered.

As stated, the units illustrated in FIG. 1 are in metric units, however, it can be seen that other units of mass and volume could be used in carrying out the present invention i.e. ounces and cubic inches and other designs of a front panel can be used as will later be understood.

Figure 2:
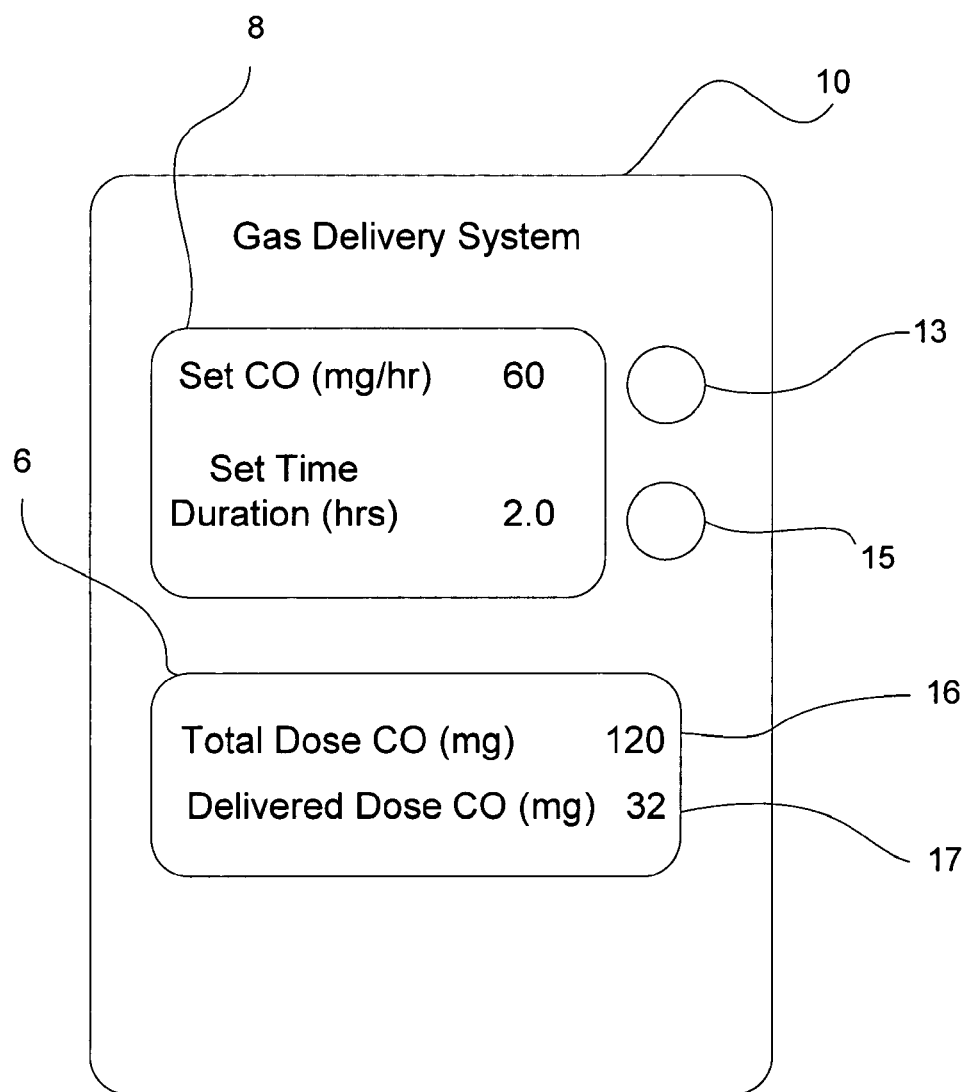

Referring to FIG. 2, there is shown a similar front panel 10 for the apparatus as shown in FIG. 1 but illustrating a different user setting option. The desired quantity of CO to be delivered to the patient is prescribed as a rate of delivery by means of input setting knob 13 and is in units of mg/hr of CO to be delivered. In this option, the device also allows the time duration (in hours) of treatment to be set by a means of an input setting knob 15. If required, the input setting by input setting knob 15 could be set to continuous where the dose per hour would run continuously until the user changed the setting. With these input settings, the apparatus can calculate and display the desired quantity of the pharmaceutical gas to be administered to the patient.

Also, as in FIG. 1, the front panel 10 also has a monitor display 6 which can display total dose of CO (mg) to be delivered (shown at 16) as calculated by multiplying the dosage/hr by the total time duration (hr.). Once the desired quantity of pharmaceutical gas has been set on the device, the system then determines the amount of pharmaceutical gas to be delivered in each breath and the amount of time and/or the number of breaths that it will take to deliver the total desired quantity of drug. As before, the monitor display 6 can display a running total of the delivered dose of CO (mg) (shown at 17) as it is delivered to the patient so the user can monitor the progress of the treatment. This can be updated each breath as more pharmaceutical gas is delivered.

As can be appreciated, FIGS. 1 and 2 illustrate two of the many options for setting the desired quantity and duration of pharmaceutical gas therapy. These options are not meant to be exhaustive and there are other setting options described or that can be understood from the detailed descriptions that follow.

Once the desired quantity of gaseous drug has been set on the device, the gas control system can then determine the amount of pharmaceutical gas to be delivered in each breath and the amount of time and/or the number of breaths that it will take to deliver the desired quantity of pharmaceutical gas.

There are a number of different approaches that the gas control system can use to determine the amount per breath and how long to deliver that dose so the desired quantity of pharmaceutical gas is delivered independent of the respiratory pattern of the patient:

a) The user can set the quantity of pharmaceutical gas to be delivered during each breath ($M_{CO}$ breath) and the gas control system calculates the number of breaths ($n_{breaths}$) which will be required to deliver the total quantity of pharmaceutical gas ($M_{CO}$) i.e.

$$n_{breaths} = M_{CO}/M_{CO\ breath} \quad (5)$$

Once the total number of breaths ($n_{breaths}$) required has been determined the value can be displayed on the front panel 12 by means of display 16 to inform the user of the number of breaths.

b) The user can set the number of breaths ($n_{breaths}$) that will administer the total quantity of the pharmaceutical gas and the system calculates the amount per breath ($M_{CO\ breath}$) to be delivered.

$$M_{CO\ breath} = M_{CO}/n_{breaths}\ (mg) \quad (6)$$

Once the amount per breath ($M_{CO\ breath}$) to be delivered has been determined, the value can be displayed on the front panel 10 to inform the user of the amount.

(c) The user could set the time duration for which the treatment is to be delivered over. The amount per breath would then be determined by calculating the quantity per minute and then, by monitoring the patients respiration rate in breaths per minute, the amount of breath can be calculated. This calculation can be repeated after every breath so any changes in the patients respiratory rate does not affect the overall quantity of gaseous drug being delivered.

d) If the desired quantity of pharmaceutical gas was entered as a dose per Kg of the patient's ideal body weight (µg/kg) along with the patient's ideal body weight (Kg) then the amount per breath ($M_{CO\ breath}$) can be determined as a function of the patient's ideal body weight (IBW), the set dose per kilogram ($M_{kg}$) and the patient's monitored respiratory rate (RR) or combinations thereof;

$M_{CO}$ breath=f (IBW, $M_{kg}$, RR) and the number of breaths can then be calculated as;

$$n_{breaths} = M_{CO}/M_{CO\ breath} \quad (7)$$

Once the amount per breath ($M_{CO}$ breath) and the number of breaths ($n_{breaths}$) required to be delivered has been determined, the values can be displayed on the front panel 10 to inform the user of the amounts the device has selected.

e) Instead of the ideal body weight (IBW) of the patient, the height and sex of the patient could be entered (which is how IBW is determined).

f) If the desired quantity of pharmaceutical gas per unit of time is entered into the device, then the device can calculate the quantity per breath to be delivered to the patient based on the current monitored respiratory breath rate (as determined by the breath trigger sensor). This quantity per breath can be recalculated after every breath when new information on the respiratory rate is available to ensure the quantity per unit of time is maintained even if the patient respiratory breath pattern changes over time.

g) There are also other ways of varying the quantity of pharmaceutical gas delivered per breath to ensure the quantity per unit of time is maintained even if the patients respiratory rate changes. As used in this specification and the appended claims, the term "varying the quantity" means that the calculated quantity is a dynamic value capable of being re-evaluated throughout administration of the therapy gas, not a fixed value. It is possible that the amount of gas delivered for each of the $n^{th}$ breaths is the same, or the amount for nearly every breath is the same. Varying the quantity does not mean that the amount of therapy gas delivered on every $n^{th}$ breath is different from the previous or subsequent breaths, merely that the value could be varied to compensate for changes in the patient's breathing pattern. For example, varying the quantity of therapy gas per breath may mean that the amount per breath is cut in half when the respiratory rate of the patient doubles.

Another example is where the device has two different amounts of delivery per breath, a high amount and a low amount. The device chooses which one to use based on the calculated quantity per unit of time being delivered over the past number of breaths. If the amount per unit of time is greater than required, it uses the low amount per breath until the situation corrects itself; likewise, if the quantity per unit of time is running low, then the unit switches to the high amount per breath.

The device can also have programmed limits which restrict the maximum and minimum values that can be selected for $M_{CO}$ breath so that the system doesn't select inappropriately too high or too low values. These limits can be set to vary based on the patient's ideal body weight, or other indicator of the patient size such as the patient's height, or the respiratory rate of the patient.

The aforesaid information is sufficient for the system of the present invention to deliver the dose to the patient and to determine the amount per breath, time of administration or other parameter in order to commence the administration of CO and to terminate that administration when the user set quantity of the pharmaceutical gas has been delivered to the patient.

Figure 3:
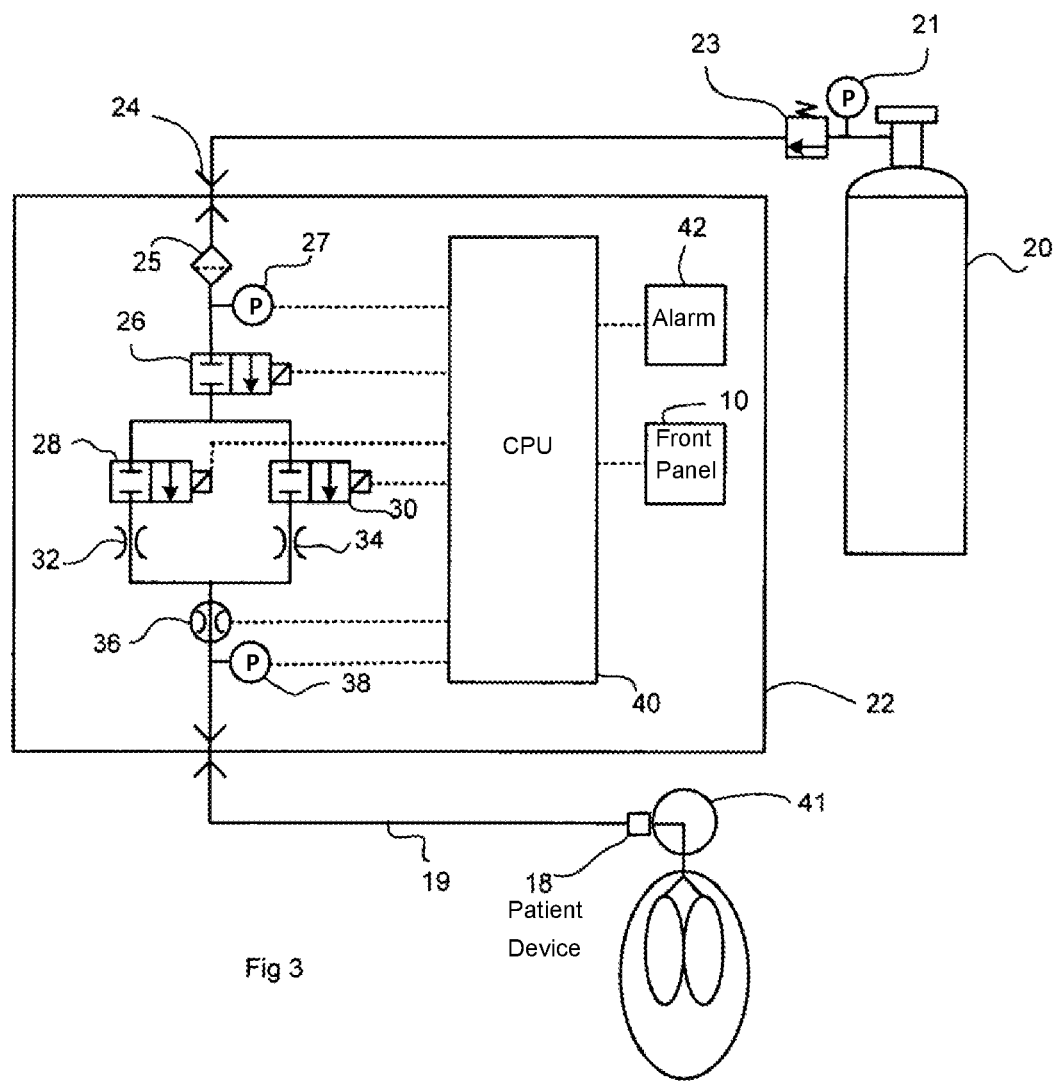
FIG. 3 is a schematic view of the present invention used with a spontaneously breathing patient.

Turning now to FIG. 3, there is shown a schematic of a system that can be used to carry out the present invention when the patient is breathing spontaneously. As can be seen, there is a patient device 18 that delivers the dosage of the pharmaceutical gas from the gas delivery system 22 to the patient 41 via a gas conducting conduit 19. As indicated, the patient device 18 can be any one of a variety of devices that actually directs the pharmaceutical gas into the patient and may be a nasal cannula, a mask, an endotracheal tube and the like.

With the FIG. 3 embodiment, there is a source of the pharmaceutical gas by means of a gas supply tank 20 containing the pharmaceutical gas generally in a carrier gas. When the pharmaceutical gas is carbon monoxide, for example, the conventional, commercially available carrier gas is air. The supply of carbon monoxide and air is provided in concentrations of 3000 ppm however, concentrations within the range of 1000 to 5000 ppm of CO in air are also possible alternatives. In the case of NO as the pharmaceutical gas, the carrier gas is conventionally nitrogen and the typical available concentrations range from 100 ppm to 1600 ppm.

Accordingly, from the supply tank 20, there is a tank pressure gauge 21 and a regulator 23 to bring the tank pressure down to the working pressure of the gas delivery system 22. The pharmaceutical gas enters the gas delivery system 22 through an inlet 24 that can provide a ready connection between that delivery system 22 and the supply tank 20 via a conduit. The gas delivery system 22 has a filter 25 to ensure no contaminants can interfere with the safe operation of the system and a pressure sensor 27 to detect if the supply pressure is adequate and thereafter includes a gas shut off valve 26 as a control of the pharmaceutical gas entering the delivery system 22 and to provide safety control in the event the delivery system 22 is over delivering the pharmaceutical gas to the patient. In the event of such over delivery, the shut off valve 26 can be immediately closed and an alarm 42 sounded to alert the user that the gas delivery system has been disabled. As such, the shut off valve 26 can be a solenoid operated valve that is operated from signals directed from a central processing unit including a microprocessor.

Downstream from the shut off valve 26 is a flow control system that controls the flow of the pharmaceutical gas to the patient through the patient device 18. In the embodiment shown, the flow control system comprises a high flow control valve 28 and a low control valve 30 and just downstream from the high and low flow control valves 28, 30, respectively, are a high flow orifice 32 and a low flow orifice 34 and the purpose and use of the high and low flow valves 28, 30 and the high and low flow orifices 32, 34 will be later explained. A gas flow sensor 36 is also located in the flow of pharmaceutical gas to the patient device 18 and, as shown, is downstream from the flow control system, however, the gas flow sensor 36 may alternatively be located upstream of the flow control system.

Next, there is a patient trigger sensor 38. When the patient breathes in during inspiration it creates a small sub atmospheric pressure in the nose or other area where the patient device 18 is located, and hence in the patient device 18 itself. The patient trigger sensor 38 detects this pressure drop and provides a signal indicative of the start of inspiration of the patient. Similarly, when the patient breathes out there is a positive pressure in the patient device 18 and the patient trigger sensor 38 detects that positive pressure and provides a signal indicative of the beginning of expiration. This allows the patient trigger sensor 38 to determine not only the respiratory rate of the patient but also the inspiratory and expiratory times.

Finally there is a CPU 40 that communicates with the patient trigger sensor 38, the high and low flow valves 28, 30, the gas shut off valve 26 and other components in order to carry out the purpose and intent of the present invention. The CPU 40 may include a processing component such as a microprocessor to carry out all of the solutions to the equations that are used by the gas delivery system 22 to deliver the predetermined quantity of the pharmaceutical gas to a patient. The CPU 40 is connected to the front panel 10 where the user can enter settings and monitor therapy.

The use of the delivery system 22 of the present invention for spontaneous breathing can now be explained. When the delivery system 22 detects by means of the patient trigger sensor 38 that inspiration has started, there is a signal that is provided to the CPU 40 to deliver a dose of a pharmaceutical gas ($M_{CO}$ breath) into the patient's inspiratory gas flow, preferably during the first ½ of the inspiratory cycle. This amount per breath has been determined based on the desired quantity of pharmaceutical gas that has been set on the system and the calculations made in a) to g) described earlier.

The actual volume of gas delivered during the breath depends on the concentration of the pharmaceutical gas in the carrier gas that is supplied by the supply tank 20. A typical source concentration ($C_{CO}$) for CO would be 3000 ppm (range 500 to 5000). The volume of source gas ($V_d$) per breath to provide a dose per breath ($M_{CO}$ breath) when the source of CO is 3000 ppm is given by the following equation, combining equations 2, 3, 4 and 6;

$$V_d = M_{CO\ breath}/(28 \cdot C_{CO} \cdot 4.16 \cdot 10^{-11}) \quad (8)$$

Given that $M_{CO}=60\times10^{-3}$ (g), $C_{CO}=3000$ (ppm), $n_{breaths}=600$, then $V_d=28.6$ (mL).

To deliver the volume of source gas per breath ($V_d$), that is, the pharmaceutical gas and the carrier gas, the delivery system 22 opens a flow control valve, such as high flow valve 28 or low flow valve 30 to allow the gas to flow to the patient until the volume per breath ($V_d$) has been delivered. The presence of the high flow orifice 32 and the low flow orifice 36 limits the flow of gas to a fixed set level during the period that the high or low flow valves 28, 30 are open so the delivery system 22 can determine the period of time the high or low flow valves 28, 30 should be open to deliver the volume per breath ($V_d$) required. Also, as another option, the flow can be determined by the gas flow sensor 36 to monitor the gas flow to the patient device 18 and thus to the patient and can shut off the appropriate high or low flow control valve 28, 30 when the desired predetermined quantity of pharmaceutical gas dose has been delivered to the patient.

As can be seen, to provide enough range to cover all the possible doses, the use of multiple flow valves, that is, the high flow valve 28 and the low flow valve 30 along with corresponding multiple orifices, high flow orifice 32 and low flow orifice 34, can be used in parallel so as to provide high and low ranges of gas flow. For instance, the low flow gas flow through the low flow valve 30 could be set to 1 L/min and the high flow gas flow through the high flow control valve 28 could be set to 6 L/min. The flow range of the particular gas flow valve is selected to ensure that the volume of gas per breath ($V_d$) can be delivered to the patient in at least ½ the inspiratory time.

As an example, if the patient was breathing at 12 breaths per minute and had an I:E ratio of 1:2 then the inspiratory time would be 1.66 seconds and half that would be 0.83 seconds.

The time (t) taken to deliver a $V_d$ of 28 mL can be calculated as follows.

$$t = V_d 60/(Q \cdot 1000) \text{ (secs)} \quad (9)$$

When Q (the flow of gas when the high flow valve 28 is open)=6 L/mins t=0.28 (secs).

That time is therefore well within ½ the inspiratory time allowed of 0.83 seconds.

The delivery system 22 can also include monitoring and alarm features to alert the user if the delivery system 22 is not working correctly. Those alarm conditions can be determined by the CPU 40 and the alarm 42 activated to alert the user to the particular fault condition. The alarm 42 can be audible, visual or both and the alarm conditions can be any one or all of the following: no breath detected, low source gas pressure, inaccurate delivery of the volume per breath ($V_d$), over delivery of the volume per breath ($V_d$), under delivery of the volume per breath ($V_d$) and termination/completion of the delivery program.

Under certain conditions, such as when the delivery system 22 is over delivering the pharmaceutical gas, the CPU 40 may signal the gas shut off valve 26 and immediately cease any further delivery of the pharmaceutical gas and the alarm 42 also activated.

The use of the alarm 42 can also be an alternative to actually shutting off the supply of the pharmaceutical gas to a patient when the predetermined desired quantity of pharmaceutical gas has been fully delivered to the patient. In such case, as an alternative to ceasing the further supply of the pharmaceutical gas to the patient, the delivery system 22 may, by means of the CPU 40, activate the alarm 42 to alert the user that the total predetermined desired quantity of the pharmaceutical gas has been delivered. The user can then determine whether to manually deactivate the delivery system 22 or continue the delivery of the pharmaceutical gas under more watchful control of the patient's status.

Figure 4:
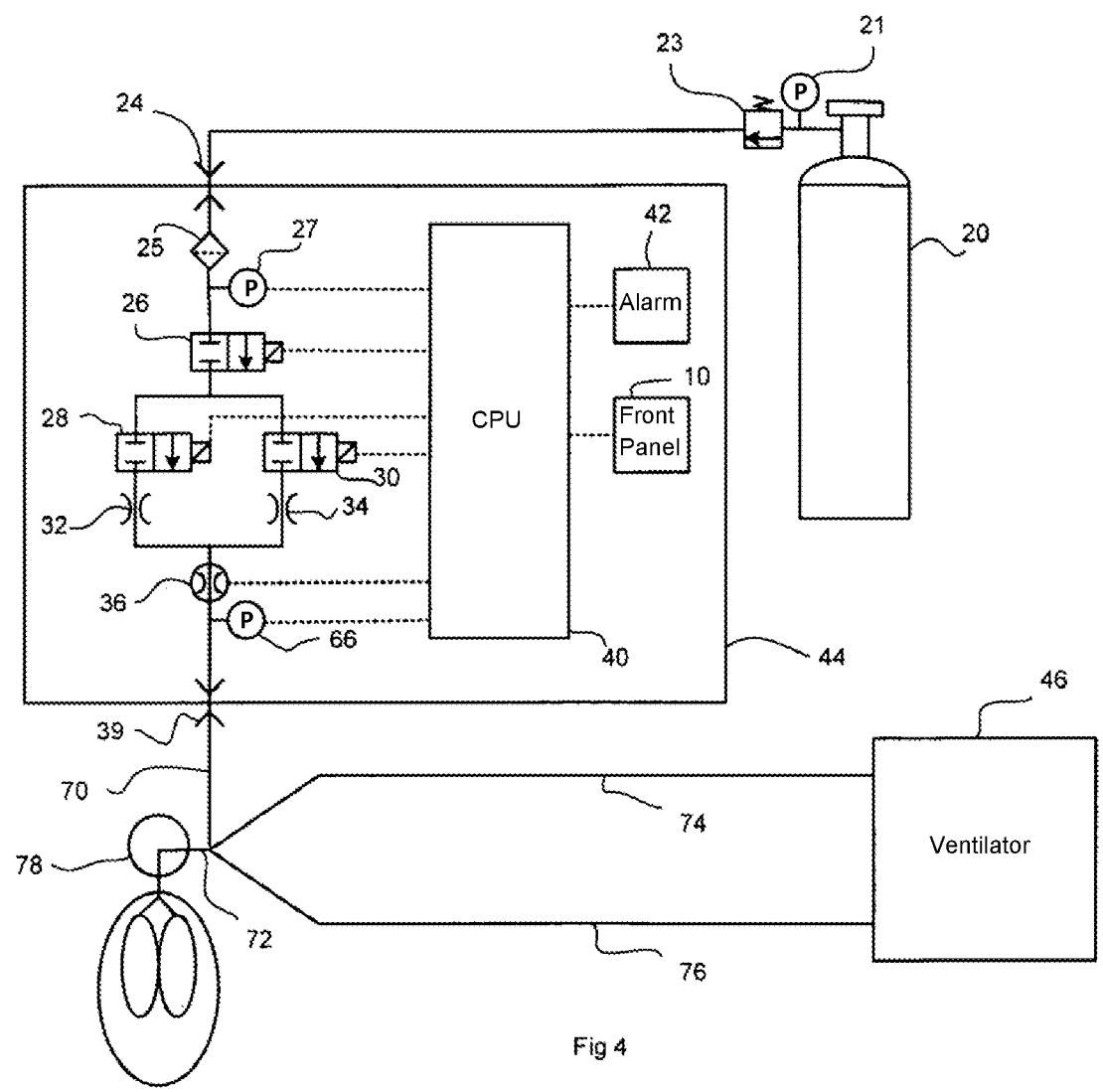
FIG. 4 is a schematic view of the present invention used with a patient being breathed by means of a ventilator.

Turning now to FIG. 4, there is shown a schematic view of a gas delivery system 44 used in conjunction with a patient being breathed by a ventilator 46. In the FIG. 4 embodiment, again there is a supply tank 20 that includes a conventional gas regulator 23 and pressure gauge 21 to supply the pharmaceutical gas along with the carrier gas to an inlet 24 in the gas delivery system 44. Briefly summarizing the components of the FIG. 4 embodiment, since they are basically the same components as described with respect to the FIG. 3 embodiment, there can be a filter 25 and a pressure sensor 27 in the gas delivery system 44. Again there is a shut off valve 26 to control the overall flow of the pharmaceutical gas through the gas delivery system 44.

The high and low flow control valves 28 and 30 control the flow of the pharmaceutical gas through the gas delivery system 44 and, the high and low flow valves 28, 30 operate as described with respect to the FIG. 3 embodiment with high and low flow orifices 32, 34 located downstream of the flow control valves.

Again there is a gas flow sensor 36 and a patient trigger sensor 66, both of which communicate with the CPU 40. With this embodiment, however, the pharmaceutical gas is carried through an outlet conduit 70 to a patient device 72 that also receives the breathing gas from the ventilator 46. As such, the ventilator 46 delivers a flow of gas through the inspiratory limb 74 and gas is returned to the ventilator 46 through the expiratory limb 76.

The flow of gas from the ventilator 46 is thus supplemented by the flow of pharmaceutical gas from the gas delivery system 44 where that gas is mixed at or proximate to the patient device 72 for introduction into the patient 78. Since all of the pharmaceutical gas is still delivered to the patient over the plurality of breaths, basically the CPU 40 can carry out the same determination of flows and the like as explained with respect to the FIG. 3 embodiment. The main difference between this FIG. 4 embodiment, and that shown in FIG. 3 is that the patient trigger sensor 66 is designed to operate in a way that works with a ventilator 46.

For instance, when the ventilator 46 provides gas flow to a patient during inspiration, it causes a positive pressure in the breathing circuit. The positive pressure is conducted through the outlet conduit 70 and is detected by the patient trigger sensor 66 and is recognized as the start of inspiration. This is the opposite to the embodiment of FIG. 3 where the patient breathes spontaneously and a negative pressure is generated during inspiration in the patient device 18; this negative pressure is conducted to the patient trigger sensor 38 of FIG. 3 and is recognized as the start of inspiration. As can be appreciated, the patient trigger sensor 38 of FIG. 3 and the patient trigger sensor of FIG. 4 could be the same pressure sensor and the gas delivery system 44 can be set for work with a ventilator or a spontaneously breathing patient.

One or more embodiments of the invention are directed to methods of administering a therapy gas to a patient. A desired total quantity of therapy gas to be administered to the patient over a period of time over a plurality of breaths is determined. The desired total quantity of therapy gas can be measured in any suitable units including, but not limited to, mass of therapy gas, mass of the therapy gas active ingredient and moles of the therapy gas active ingredient. The desired total quantity of therapy gas to be administered to the patient can be entered directly into the device or can be calculated by the device. For example, one or more of the following parameters may be input to the device: (a) the desired total quantity of therapy gas; (b) the period of time for delivery of the therapy gas; (c) the total number of breaths over which the delivery gas is delivered; and (d) the frequency of administration, i.e. choose the value of n such that the therapy gas is delivered every $n^{th}$ breath, wherein n is 1 or greater. Treatment may be repeated as necessary. It will be understood by those skilled in the art that other parameters may be entered.

The quantity of the therapy gas is delivered to the patient during inspiration. In one or more embodiments, the therapy gas is delivered to the patient's alveoli. In specific embodiments, substantially all of the therapy gas is delivered to the patient's alveoli. As used in this specification and the appended claims, the term "substantially all" means that at least about 80%, 85%, 90% or 95% of the therapy gas is delivered to the alveoli. In some embodiments, "substantially all" means that a sufficient percentage of therapy gas is delivered to the alveoli so that there is little or no irritation of the respiratory track.

Delivery of the therapy gas to the patient happens every $n^{th}$ breath during the plurality of breaths. In detailed embodiments, n is 1 or greater. When n is 1, the therapy gas is delivered to the patient on each breath. Where n is 2, the therapy gas is delivered to the patient on every other breath. In various embodiments, n is 1, 2, 3, 4, 5, 6, 7, 8, 9 or 10. Thus, when n is 2 or greater, conditions of skipped breathing are achieved, meaning therapy gas is skipped on certain breaths while administered on certain other breaths. Additionally, the interval between delivery breaths can vary throughout the delivery of the total quantity depending on a number of conditions. For example, therapy gas may be delivered on breaths 1, 3, 5, 8, 10, 12, etc. In detailed embodiments, the administration of the therapy gas is repeated for each $n^{th}$ breath. In various embodiments, the therapy gas is delivered for 2 out of every 3 breaths, or for 3 out of every 5 breaths, or for 4 out of every 7 breaths, or for 2 out of every 5 breaths, or for 2 out of every 7 breaths, etc.

Furthermore, certain embodiments provide that the delivery every $n^{th}$ breath does not need to follow a specific pattern. For example, as discussed in more detail below, certain breaths may be skipped for a variety of reasons, such as an amount to be delivered in a particular breath being less than a minimum delivery quantity. Breaths may also be skipped such that the gas is not delivered on literally every $n^{th}$ breath, but the therapy gas is delivered on average every $n^{th}$ breath. Also, the value of n may change during administration such that the therapy gas is delivered is every $n_1^{th}$ breath for part of the administration, the therapy gas is delivered is every $n_2^{th}$ breath for another part of the administration, the therapy gas is delivered every $n_3^{th}$ breath for a third part of the administration, etc.

In some embodiments, the quantity of therapy gas provided at the $n^{th}$ breath is a function of one or more of a first respiratory rate, a first tidal volume of the patient and the patient's ideal body weight. The first respiratory rate and tidal volume can be measured prior to, at the beginning of, or during the treatment. One or more of the first respiratory rate and tidal volume can be used to calculate an initial amount of therapy gas to be delivered on each $n^{th}$ breath for a period of time to deliver the desired total quantity of therapy gas. After this initial respiratory rate is measured and the initial amount to be delivered per $n^{th}$ breath is calculated or determined, changes in the respiratory rate may occur and the calculated amount may need to be adjusted. Thus, a subsequent calculation of the amount of therapy gas to be delivered can be performed. The subsequent calculation can be done after any or all individual administration of therapy gas. In one embodiment, the amount of therapy gas to be delivered during the $n^{th}$ breath can be recalculated after each individual delivery. As a result of the recalculations, the total quantity of therapy gas delivered is independent of the patient's respiratory rate, and the total quantity of therapy gas can be controlled to be the desired amount.

As an example, should the initial amount of therapy gas to be delivered during the $n^{th}$ breath be calculated to amount to 100 µL, and after the first breath, the patients respiratory rate doubles, the subsequent calculated rate would be about 50 µL per $n^{th}$ breath. In the prior art, which does not recalculate the amount of therapy gas to be delivered, this scenario would result in the patient having received about twice the amount of therapy gas as was originally intended by the end of the period of time for delivery of the gas. Thus, recalculating the amount of gas to be delivered throughout the delivery period may result in a more accurate amount of therapy gas provided to the patient and can help mitigate potential side effects of too much of the therapy gas. Accordingly, varying the amount per $n^{th}$ breath ensures that the desired total amount of therapy gas is delivered to the patient over the plurality of breaths.

The quantity of the therapy gas per $n^{th}$ breath can be varied to ensure that the desired total quantity over the period of time is administered, independent of the respiratory pattern of the patient. The quantity of therapy gas delivered may be in the range of a minimum quantity and a maximum quantity. In detailed embodiments, the minimum quantity and maximum quantity are functions of the device delivering the therapy gas. The minimum quantity may be the smallest amount that the device is capable of providing and the maximum quantity may be the maximum amount that the device is capable of providing. For example, if the smallest volume of therapy gas that the device is capable of releasing is 10 µL, then the concentration of the therapy gas multiplied by the smallest deliverable volume will give the smallest amount of therapy gas active that can be delivered.

In some embodiments, when the quantity of therapy gas to be delivered per $n^{th}$ breath is greater than the minimum quantity and less than the maximum quantity, the quantity of therapy gas per breath is administered on the $n^{th}$ breath. When the quantity of therapy gas per $n^{th}$ breath is less than the minimum, the therapy gas can be administered in many ways. For example, if the device is only capable of delivering a minimum of 10 µL, but the quantity to be delivered is 8 µL, the device can skip the amount to be delivered during this breath and add the amount (8 µL) to any of the subsequent breaths, or can divide the amount among two or more subsequent breaths. Alternatively, the device can deliver the minimum amount to be delivered (10 µL) and subtract the difference (2 µL) from a subsequent breath or divided the amount to be subtracted over two or more subsequent breaths. In detailed embodiments, the quantity of therapy gas per breath is skipped and a new quantity of therapy gas per breath is calculated for subsequent doses. The new quantity can include the skipped amount in a single breath, or the new quantity can spread the skipped amount over multiple breaths.

When the quantity of therapy gas to be delivered for the $n^{th}$ breath is greater than the maximum quantity, several potential courses of action can be taken, including triggering an alarm. In detailed embodiments, the maximum quantity of therapy gas per breath is administered and the difference between the calculated quantity of therapy gas for the $n^{th}$ breath and the maximum quantity of therapy gas is carried forward for later delivery on one or more subsequent breaths. However, where later delivery is not possible, the system may trigger one of many alarm conditions or can be set to automatically extend the period of time for delivery to ensure that the desired total amount of therapy gas is delivered.

In some embodiments, n is 1 such that the therapy gas is administered every breath. However, even if the therapy gas is set to be administered every breath, some breaths may be skipped if the amount to be delivered in a given breath is less than the minimum quantity. As noted above, the quantity that would have been delivered during this skipped breath may be added to any of the subsequent breaths or may be divided among two or more subsequent breaths.

In some embodiments, the therapy gas is administered every $n^{th}$ breath where n is 2 or greater. This means that the therapy gas is provided in a "skip breathing" regimen. Skip breathing may be desired as there can be an overall decrease in the amount and severity of adverse reactions including irritation due to the therapy gas. In some embodiments, where n is 2 or greater, the therapy gas is delivered during every other (for n=2) breath, or greater, and no therapy gas is administered during the other breaths. During the alternate breaths (i.e., where no therapy gas is provided) the patient can breathe ambient air, oxygenated air, pure oxygen, or a different therapy gas, depending on the desired treatment. In detailed embodiments, the patient breathes ambient air on inhalations not accompanied by therapy gas.

In some embodiments, where n is 2 or greater, the administration of quantities greater than the maximum amount can be handled differently than when therapy gas is delivered on every breath. If the amount to be delivered is greater than the maximum, the device may proceed in one or more of the following manners: (a) an alarm can be activated; (b) the maximum amount of therapy gas that can be delivered is delivered to the patient on the $n^{th}$ breath; and (c) the difference between the maximum amount and the quantity to be delivered is carried over to subsequent breaths or administrations. If the following breath is skipped as part of a skip breathing protocol, i.e. is not an $n^{th}$ breath, the carryover dose could be provided during the skipped breath or maintained until the next breath scheduled for dosing.

The amount of therapy gas to be delivered can be calculated multiple times during the total administration time. The amount can be recalculated based on the number of breaths, the amount of time between measurements and after every breath, as desired by the administration protocol. When the quantity of the therapy gas to be delivered is skipped, for any reason, a new quantity of therapy gas per breath is calculated.

Upon completion of the administration program, one or more of several actions can be taken by the device. The device can trigger an alarm, as described earlier. The administration can continue until manually or programmatically stopped. The delivery program (i.e., the amount of therapy gas per period of time) can be repeated for any number of repetitions, or indefinitely. The administration of the therapy gas can be stopped until manually or programmatically restarted (i.e., a programmed pause between executions of the administration protocol). For example, if the program calls for delivery over a one hour period, the device can be programmed to wait for a specified period (e.g., 2 hours) after completion before restarting the administration program.

Additional embodiments of the invention are directed to methods of treating pulmonary arterial hypertension (PAH), including those suffering from chronic obstructive pulmonary disease (COPD), idiopathic pulmonary fibrosis (IPF), etc. A desired total quantity of therapy gas to be delivered to a COPD patient over a period of time over a plurality of breaths is determined. The quantity is administered to the patient during inspiration every $n^{th}$ breath of the plurality of breaths, where n is 2 or greater. The quantity of therapy gas is varied per breath to ensure that the desired total quantity delivered over the period of time is maintained independent of the respiratory pattern of the patient. In detailed embodiments, varying the quantity of the therapy gas per breath comprises determining the quantity of therapy gas to be delivered during the breath based on the respiratory rate of the patient and the amount of therapy gas already given to the patient. In other words, the desired total amount of therapy gas to be delivered to the patient over the plurality of breaths is ensured by varying the amount delivered per breath, as required by changes in the breathing pattern of the patient.

Figure 5:
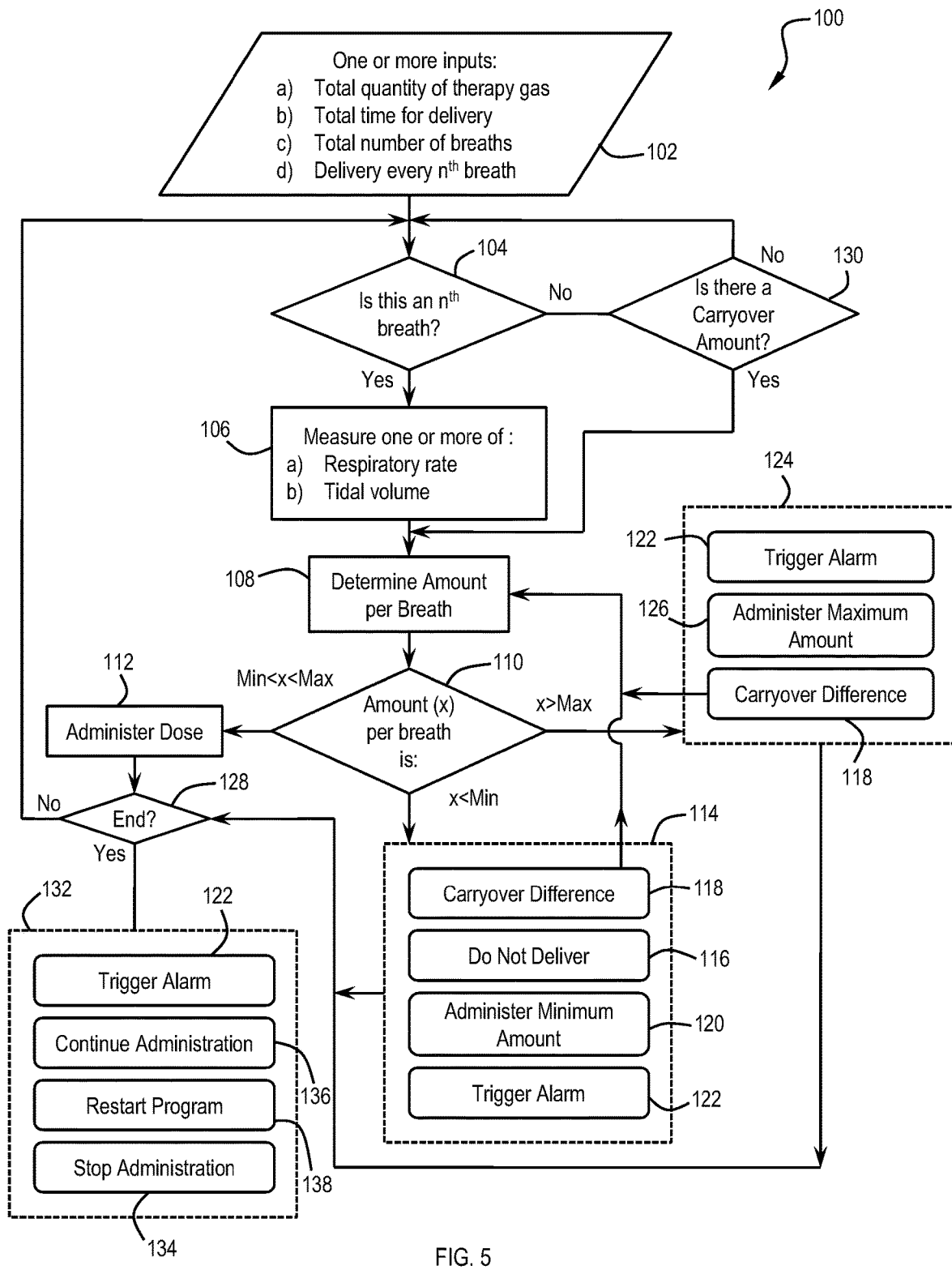
FIG. 5 shows a flowchart of an exemplary method of administering a therapy gas to a patient according to one or more embodiments of the invention.

FIG. 5 shows a flowchart for a detailed method 100 in accordance with one or more embodiments of the invention. It will be understood by those skilled in the art that the method outlined in FIG. 5 is merely a possible methodology and should not be taken as limiting the scope of the invention. The methods described provide for ability to manage the total quantity of therapy gas given over a period of time. Pertinent information related to the administration of the therapy gas and the program conditions 102 are entered into a device capable of delivering the therapy gas. The program conditions can explicitly state the necessary information for delivery, or can provide variables which the device can use to calculate the necessary information.

The device determines if the approaching breath is an $n^{th}$ breath 104, meaning that the device will administer the therapy gas on that breath. On a first pass through the process flow, the answer will likely be yes, leading the device to determine one or more physiological parameters 106 of the patient (e.g., respiratory rate and tidal volume). The physiological parameters can be measured by the device or transferred from another measuring device or can be manually entered into the device.

Based on the measurements of the physiological parameters, the device can calculate the amount of therapy gas to be delivered to the patient 108. This can be an initial calculation or a subsequent calculation. The calculated amount of therapy gas per breath may be compared 110 to a minimum quantity and a maximum quantity of deliverable gas. The minimum and maximum quantities, as described previously, can be functions of the device, functions of the concentration of the therapy gas source, a function of the physiological parameters of the patient and combinations thereof. If the amount of therapy gas to be delivered is between the minimum and maximum quantities, the dose of therapy gas is delivered 112 to the patient on the next breath.

If the comparison in 110 indicated that the amount of therapy gas to be delivered is less than the minimum deliverable amount, the device can proceed with any or all of several below minimum amount options 114. The device can withhold administration 116 of the therapy gas for that breath. The device can carryover 118 the amount not administered to one or more subsequent breaths. The minimum amount can be administered 120 resulting in an over-administration for that breath. The amount over-administered can then be reduced from one or more subsequent breaths. An alarm condition 122 (e.g., audible, visual, or electronic), as described earlier, can be activated.

If the comparison in 110 indicates that the amount of therapy gas to be delivered is greater than the maximum deliverable amount, the device can proceed with any or all of several above maximum amount options 124. The device can trigger an alarm condition 122 as described above. The device can administer the maximum amount 126 and either discard the difference or carryover 118 the difference to subsequent breaths. However, depending on the reason for the quantity to be delivered to be over the maximum and the administration protocol, carrying over the difference to subsequent breaths can result in the amount for each $n^{th}$ breath to be over the maximum. To avoid this, the device can be programmed to carryover the amount if, for example, the calculated amount to be delivered is an outlier or if subsequent breaths are skipped.

After the amount of therapy gas is delivered (if applicable), the device determines if it has reached the end conditions 128 of the program (e.g., time, amount delivered, number of breaths). If the end condition has not been reached, the device can then check to see if the next breath is scheduled to receive a dose of therapy gas 104. If yes, the method proceeds through one or more of the steps as previously described. If the following breath is not supposed to receive therapy gas, the device can determine if there is carryover from a previous breath 130. If there is carryover and it is the delivery of therapy gas is allowed on the alternate breaths, the device can determine the amount of therapy gas per breath to deliver 108. This can be as simple as delivering the carried over amount, or holding the amount for further subsequent breaths. If there are no carry over breaths 130, the device can do nothing for the breath and restart the method at evaluating if the next breath is an $n^{th}$ breath 104.

When the end conditions 128 have been met, the method and device can proceed through one or more of various end condition actions 132. The delivery of the therapy gas can be discontinued until manually or programmatically restarted 134. An alarm can be triggered. Administration of the therapy gas can continue 136 under the same conditions (e.g., restarting the program 138) or with different conditions.

Those skilled in the art will readily recognize numerous adaptations and modifications which can be made to the pharmaceutical gas delivery system and method of delivering a pharmaceutical gas of the present invention which will result in an improved method and system for introducing a known desired quantity of a pharmaceutical gas into a patient, yet all of which will fall within the scope and spirit of the present invention as defined in the following claims. Accordingly, the invention is to be limited only by the following claims and their equivalents.

What is claimed is:

1. A method of administering a pharmaceutical gas to a patient, wherein the pharmaceutical gas comprises at least one of nitric oxide or carbon monoxide, the method comprising:
   delivering a first quantity of the pharmaceutical gas to the patient in a first breath;
   monitoring the patient's respiratory rate or changes in the patient's respiratory rate;
   varying the quantity of pharmaceutical gas delivered to the patient in one or more subsequent breaths based on the monitored respiratory rate or changes in the patient's respiratory rate.

2. The method of claim 1, wherein the quantity delivered in the subsequent breath is greater than the first quantity in response to a decrease in the patient's respiratory rate.

3. The method of claim 1, wherein the quantity delivered in the subsequent breath is less than the first quantity in response to an increase in the patient's respiratory rate.

4. The method of claim 1, wherein varying the quantity of pharmaceutical gas delivered to the patient avoids high unsafe doses or doses too low to be effective.

5. The method of claim 1, wherein the pharmaceutical gas is delivered to the patient every breath.

6. The method of claim 1, wherein the pharmaceutical gas is delivered to the patient every nth breath, wherein n is 1 or greater.

7. The method of claim 1, wherein at least one breath is skipped such that pharmaceutical gas is not administered during the breath.

8. The method of claim 7, wherein when the breath is skipped, a new quantity of pharmaceutical gas per nth breath is calculated.

9. The method of claim 1, wherein when the quantity of pharmaceutical gas to be delivered in a breath is greater than a maximum quantity of pharmaceutical gas per breath, the maximum quantity of pharmaceutical gas per breath is administered and the difference between the quantity of pharmaceutical gas to be delivered in the breath and the maximum quantity of pharmaceutical gas per breath is added to one or more subsequent breaths.

10. The method of claim 1, wherein one or more of the first quantity and the quantity delivered in the subsequent breath is delivered during the first half of inspiration.

11. A gas delivery system comprising:
   an inlet to connect to a source of pharmaceutical gas comprising at least one of nitric oxide or carbon monoxide;
   an outlet to connect to a device that introduces the pharmaceutical gas to a patient;
   a breath trigger sensor to measure a patient's respiratory rate; and
   a gas control system in communication with the breath trigger sensor that delivers a varying quantity of pharmaceutical gas to the patient based on changes in the patient's respiratory rate.

12. The system of claim 11, wherein a quantity delivered in a subsequent breath is greater than a quantity delivered in a previous breath in response to a decrease in the patient's respiratory rate.

13. The system of claim 11, wherein a quantity delivered in a subsequent breath is less than a quantity delivered in a previous breath in response to an increase in the patient's respiratory rate.

14. The system of claim 11, wherein the gas control system delivers the quantity of pharmaceutical gas during the first half of the patient's inspiratory cycle.

15. The system of claim 11, wherein the gas control system delivers the pharmaceutical gas to the patient every breath.

16. The system of claim 11, wherein delivering a varying quantity of pharmaceutical gas to the patient avoids high unsafe doses or doses too low to be effective.

17. The system of claim 11, wherein the pharmaceutical gas is delivered to the patient every nth breath, wherein n is 1 or greater.

18. The system of claim 11, wherein at least one breath is skipped such that pharmaceutical gas is not administered during the breath.

19. The system of claim 18, wherein when the breath is skipped, a new quantity of pharmaceutical gas per nth breath is calculated.

20. The system of claim 11, wherein when a quantity of pharmaceutical gas to be delivered in a breath is greater than a maximum quantity of pharmaceutical gas per breath, the maximum quantity of pharmaceutical gas per breath is administered and the difference between the quantity of pharmaceutical gas to be delivered in the breath and the maximum quantity of pharmaceutical gas per breath is added to one or more subsequent breaths.

* * * * *